United States Patent [19]

Lee et al.

[11] Patent Number: 5,266,475

[45] Date of Patent: Nov. 30, 1993

[54] GLUCOSE ISOMERASES WITH IMPROVED AFFINITY FOR D-GLUCOSE

[75] Inventors: Chanyong Lee, San Francisco, Calif.; Michael Bagdasarian, Haslett, Mich.; J. Gregory Zeikus, Okemos, Mich.; Menghsiao Meng, East Lansing, Mich.

[73] Assignee: Michigan Biotechnology Institute, Lansing, Mich.

[21] Appl. No.: 762,681

[22] Filed: Sep. 19, 1991

[51] Int. Cl.$^5$ ............................................. C12N 9/92
[52] U.S. Cl. ................... 435/234; 435/842; 935/10; 935/14
[58] Field of Search ........................................ 435/234

[56] References Cited

U.S. PATENT DOCUMENTS

| | | | |
|---|---|---|---|
| 4,572,898 | 2/1986 | Zeikus | 435/200 |
| 4,628,031 | 12/1986 | Zeikus et al. | 435/205 |
| 4,647,538 | 3/1987 | Zeikus et al. | 435/201 |
| 4,721,676 | 1/1988 | Zeikus | 435/252.7 |
| 4,737,459 | 4/1988 | Zeikus et al. | 435/162 |
| 4,894,331 | 1/1990 | Ratzkin et al. | 435/94 |

FOREIGN PATENT DOCUMENTS 0436502 7/1991 European Pat. Off. .
0440273 8/1991 European Pat. Off. .
9000196 1/1990 World Int. Prop. O. .

OTHER PUBLICATIONS

Schink and Zeikus, "*Clostridium thermosulfurogenes* sp. nov., a New Thermophile that Produces Elemental Sulphur from Thiosulphate," *Journal of General Microbiology* (1983), 129, 1149–1158.

Lee et al., "Catalytic Mechanism of Xylose (Glucose) Isomerase from *Clostridium thermosulfurogenes*," *Journal of Biological Chemistry* (1990), vol. 265, No. 31, pp. 19082–19090.

*Primary Examiner*—Robert A. Wax
*Assistant Examiner*—Gabriele E. Bugalsky
*Attorney, Agent, or Firm*—Quarles & Brady

[57] ABSTRACT

A genetically engineered glucose isomerase with improved affinity for D-glucose and the method of preparation of such a glucose isomerase are disclosed. The glucose isomerase is obtained by mutagenizing the gene of a naturally occurring glucose isomerase such that a smaller amino acid replaces a larger amino acid in the catalytic site. In an especially advantageous embodiment of the present invention, the Clostridium glucose isomerase sequence is mutated and the residue replaced with a smaller amino acid is either $Trp_{139}$ or $Val_{186}$.

10 Claims, 1 Drawing Sheet

|  |  | 481 |  |  |  |  |  |  |  |  |
|---|---|---|---|---|---|---|---|---|---|---|
| W.T.: |  | 3' | TGC | TTT | CAA | AAC | ACC | CCA | TGA | CGC | TTA |
|  |  |  | Thr | Lys | Val | Leu | Trp | Gly | Thr | Ala | Asn |
| Trp$_{139}$ → Phe: | 5' | ACG | AAA | GTT | TTG | TTT | GGT | ACT | GCG | AAT |
|  |  |  |  |  |  |  | Phe |  |  |  |  |
| Trp$_{139}$ → Tyr: | 5' | ACG | AAA | GTT | TTG | TAT | GGT | ACT | GCG | AAT |
|  |  |  |  |  |  |  | Tyr |  |  |  |  |

|  |  | 622 |  |  |  |  |  |  |  |  |
|---|---|---|---|---|---|---|---|---|---|---|
| W.T.: |  | 3' | CCG | CTT | TTG | ATG | CAT | AAG | ACC | CCA | CCT |
|  |  |  | Gly | Gly | Asn | Tyr | Val | Phe | Trp | Gly | Gly |
| Val$_{186}$ → Thr: | 5' | GGC | GAA | AAC | TAC | ACA | TTC | TGG | GGT | GGA |
|  |  |  |  |  |  |  | Thr |  |  |  |  |
| Val$_{186}$ → Ser: | 5' | GGC | GAA | AAC | TAC | TCA | TTC | TGG | GGT | GGA |
|  |  |  |  |  |  |  | Ser |  |  |  |  |
| Val$_{186}$ → Ala: | 5' |  | GAA | AAC | TAC | GCA | TTC | TGG | GGT |  |
|  |  |  |  |  |  |  | Ala |  |  |  |  |

FIG. 1

GLUCOSE ISOMERASES WITH IMPROVED AFFINITY FOR D-GLUCOSE

FIELD OF THE INVENTION

The present invention relates to enzymes. More particularly, the present invention relates to genetically engineered glucose isomerases.

BACKGROUND OF THE INVENTION

Commercial glucose isomerase is really a xylose isomerase (D-xylose ketol isomerase, EC 5.3.1.5), an intracellular enzyme that catalyzes the isomerization of D-xylose to D-xylulose. However, the practical significance of the enzyme stems from the fact that the xylose isomerase can use either D-xylose or D-glucose as substrates. The primary industrial use for glucose isomerase is in the synthesis of high fructose corn syrups used as sweeteners. More than 15,000 million pounds of these sweeteners are produced annually, and production levels continue to increase (1-3). Therefore, the xylose isomerase is commonly referred to as glucose isomerase. When we refer to "glucose isomerase," we are referring to the D-xylose ketol isomerase.

All glucose isomerases known and studied to date, including those used in the present industrial processes for making fructose, exhibit considerably lower $K_m$ values for their natural substrate, D-xylose, than they do for D-glucose. (A lower $K_m$ value indicates that less substrate is needed for half-maximal reaction velocity.) In addition, the maximum activity ($V_{max}$) of the enzyme for D-xylose is considerably higher than it is for D-glucose. (A higher $V_{max}$ value indicates a higher rate of reaction at a saturating substrate concentration.) It would be an advantage, therefore, in the industrial production of fructose to have glucose isomerases with increased affinity for D-glucose as a substrate.

The commercial value of glucose isomerases as a biocatalyst has stimulated research on the structure and function of the enzyme and on the organization and regulation of the glucose isomerase gene in different organisms. (1,4-9) Complete nucleotide sequences and predicted amino acid sequences have been determined for glucose isomerase from *Escherichia coli*, (10,11) *Bacillus subtilis* (12,13), *Salmonella typhimurium* (14), Ampullariella sp.(15), *Streptomyces violaceoniger* (16), *Streptomyces olivochromogenes* (7), *Streptomyces griseofuscus* (17), Arthrobacter (18) and *Clostridium thermosulfurogenes* (19,20). In addition, three-dimensional structures have been resolved for glucose isomerases from *Streptomyces rubiginosus* (21), *Streptomyces olivochromogenes* (22) and Arthrobacter strain B3728 (18,23,24). SEQ ID NO: 1 is predicted amino acid sequence of glucose isomerase from *Clostridium thermosulfurogenes*.

Comparison of these sequences demonstrates that glucose isomerases from different sources share considerable amino acid sequence homology (17,20,22). SEQ ID NO: 2 is a consensus amino acid sequence we have derived from the sequences disclosed above. An Xaa symbol in SEQ ID NO: 2 indicates a position at which there is no consensus. The consensus sequence is displayed so that the first amino acid of the consensus sequence corresponds to the first amino acid sequence of the *Clostridium thermosulfuorgenes* sequence in SEQ ID NO: 1. For the Clostridium sequence to fit the consensus sequence, an extra residue must be inserted in the Clostridium sequence after amino acid residues 68 and 419.

Therefore, similarities in the molecular structure and catalytic mechanisms should exist among glucose isomerases from different organisms. In support of this proposal, amino acid residues such as $His_{101}$, $Thr_{141}$, $Val_{186}$, and $Trp_{139}$ of the Clostridium enzyme, that were predicted by X-ray diffraction studies of the Arthrobacter enzyme to be part of the active center, and amino acid residues $Glu_{232}$ and $Glu_{268}$, that were predicted to bind metal ions essential for activity, are highly conserved in the species compared above (19-22).

It was thought initially that enzymatic isomerization of xylose and glucose proceeds via a cis-enediol intermediate and is accomplished by proton transfer with a histidine residue acting as a general base and attracting the proton from the $C_1$ hydroxyl of the substrate (6,25,26). The analogy of glucose isomerase to triose phosphate isomerase, for which the base-catalyzed enediol mechanism has been demonstrated (25), and some indications from X-ray crystallographic studies (6) seemed to support this hypothesis. The early mutagenesis studies have, therefore, been interpreted as indicating that $His_{101}$ was the residue acting as the essential base in the isomerization reaction (10).

However, glucose isomerase exhibits properties very distinct from those of triose phosphate isomerase, which argues that the two enzymes are unlikely to employ the same catalytic mechanisms. Moreover, recent crystallographic studies have indicated that the position of the substrate bound to glucose isomerase is different from the position suggested earlier and, therefore, the essential histidine residue ($His_{101}$ in the Clostridium enzyme) is positioned too far from the $C_1$ and $C_2$ atoms of the substrate to be able to attract protons from their hydroxyl groups. It was suggested instead that the isomerization proceeds via a metal-catlyzyed hydride shift and the essential histidine is required for either the ring opening or the binding of the substrate (22-24).

The ability to mutagenize a protein at a specific site has enabled scientists to verify some predictions stemming from structural analysis of glucose isomerase. For example, it has been shown that in the *E. coli* enzyme the $His_{101}$ residue is essential for enzymatic activity because when another amino acid is substituted, the resulting protein is inactive (10). The glucose isomerase from *Clostridium thermosulfurogenes* has proved to be a particularly convenient enzyme for modification by protein engineering because the gene has been expressed in both *E. coli* and a food-safe host, *B. subtilis*. The enzyme produced in these hosts could easily be purified in high yields (19). In the Clostridium enzyme, substitutions at the position of several His residues other than $His_{101}$ had no effect on enzyme activity (19).

On the other hand, substitution of $His_{101}$ by Gln, Glu, Asp or Asn resulted in mutant enzymes that retained 10-14% of the wild type activity, whereas the $K_m$ was not changed significantly. Moreover, the resulting enzymes showed a constant activity at acidic pH below 6.5 (19). This result indicated that the ability of $His_{101}$ to be protonated is essential for the activity of glucose and xylose isomerases. However, if this residue had functioned as a simple base its substitution by the non-basic amino acids, such as Gln or Asn would be expected to create an inactive enzyme. Two other possible roles for the $His_{101}$ have been suggested: (i) as a catalyst of the ring opening and (ii) as a stabilizer of the transition state (the species of the reaction pathway with the highest free energy).

Determination of the isotope effect of D-[2-$^2$H]-glucose on the $V_{max}$ of *C. thermosulfurogenes* isomerase has demonstrated that hydrogen transfer, and not ring opening, is the rate-limiting step in the isomerization reaction for both the wild type and the mutant His$_{101}$ —> Gln enzyme (20). Furthermore, the x-ray crystallographic studies of the enzyme-substrate complex revealed only the open-chain forms of the substrate bound to the enzyme crystals (21,23,24). These findings strongly suggest that this complex is the most stable species among the reaction intermediates.

Although scientists have studied the active site of glucose isomerase from many different organisms, the art of fructose synthesis still lacks a glucose isomerase with an improved affinity for D-glucose.

SUMMARY OF THE INVENTION

The present invention is a genetically engineered enzyme with an amino acid sequence corresponding essentially to that of a wild-type glucose isomerase. At least one amino acid in the catalytic site of this genetically engineered glucose isomerase has been replaced by a smaller amino acid residue. This genetically engineered enzyme exhibits an increased affinity for D-glucose.

The present invention is also a method for creating a genetically engineered glucose isomerase with improved affinity for D-glucose. This method involves isolating a naturally occuring glucose isomerase gene and mutagenizing the gene such that at least one amino acid in the catalytic site has been replaced by a smaller amino acid.

In a particularly advantageous embodiment of the present invention, the amino acid sequence of the genetically engineered glucose isomerase corresponds essentially to the Clostridium glucose isomerase, and Trp$_{139}$ residue has been replaced with either Phe or Tyr.

It is an object of the present invention to create a glucose isomerase which has a lower $K_m$ and a higher $k_{cat}$ for D-glucose than does the wild-type enzyme.

It is another object of the present invention to disclose a method for preparation of glucose isomerase in which amino acid residues that sterically hinder the binding of D-glucose to the catalytic site of the enzyme are substituted with smaller amino acid residues.

It is another object of the present invention to disclose a glucose isomerase in which the amino acid residues that in the wild type enzyme cause steric hindrance during the binding of D-glucose to the catalytic site in the enzyme are replaced with amino acid residues that do not cause as much steric hindrance.

The present invention is advantageous because the engineered glucose isomerase will more efficiently and rapidly produce fructose from D-glucose.

Other objects, advantages and features will become apparent from the following specification, drawings and claims.

DESCRIPTION OF THE DRAWINGS

FIG. 1 shows the amino acid sequences corresponding to synthetic oligonucleotide primers used for site-directed mutagenesis of the glucose isomerase gene. The wild type (W.T.) represents the coding strand of the xylA (glucose isomerase) gene inserted in the M13mp19 bacteriophage vector. The numbers refer to the published nucleotide sequence of glucose isomerase (19-20) and SEQ ID NO: 1.

DESCRIPTION OF THE PREFERRED EMBODIMENT

We compared the amino acid sequences of 8 different glucose isomerases and observed both similarities and differences in the primary structure of these enzymes. The most extensive differences are observed at the amino-terminal domain, which in the enzymes from Streptomyces and Arthrobacter is shorter than in the Clostridium enzyme by 48 amino acids. We previously noted that sequences within the domains that function as binding and catalytic sites of different glucose isomerases are highly conserved, and we expected that similarities in the primary structure of these enzymes reflect similarities in the function of the individual amino acid residue in the critical domains of the enzymes.

In the three-dimensional structure of the Arthrobacter enzyme, the residues corresponding to Trp$_{139}$ and Val$_{186}$ are presumed to be located at the border of the substrate-binding pocket (24). We posited that these residues provided the hydrophobic environment for the catalytic reaction of the hydride shift and might constitute a steric hindrance for the binding of glucose as opposed to the binding of the smaller molecule of xylose. Our method for preparing a glucose isomerase with improved affinity for D-glucose involves, in general, substituting either or both of these two residues with smaller amino acids, thereby lowering the steric hindrance to D-glucose. Although we chose to manipulate the Trp$_{139}$ and Val$_{186}$ residues, we envision that the replacement of other catalytic site residues would also provide a glucose isomerase with improved affinity for D-glucose. By "catalytic site residues," we mean those residues that are essential for the performance of the catalytic reaction.

An improved glucose isomerase is prepared by first isolating a glucose isomerase gene. We have discovered that a new, improved glucose isomerase, possessing properties superior to those of the corresponding natural enzyme, may be prepared by the genetic engineering of the Clostridium glucose isomerase gene. As disclosed above, glucose isomerase genes have been isolated and studied from many organisms. To practice the present invention, a previously isolated gene may be obtained or sequences disclosed in SEQ. ID NO: 1 may be used as a probe to isolate a glucose isomerase gene using standard molecular biology techniques. We chose to manipulate the Clostridium gene because this gene has been expressed in both *E. coli* and the food-safe host *B. subtilis*, and the enzyme produced in these hosts can be purified easily (19).

The glucose isomerase nucleotide sequence must be manipulated such that amino acids within the catalytic site are replaced with smaller amino acids. By "smaller" amino acid, we mean an amino acid with fewer atoms than the amino acid it will replace. For example, Phe is smaller than Trp, and Thr is smaller than Val.

Preferably, site-directed mutagenesis is used to modify the gene encoding the wild type enzyme, followed by the subsequent introduction of the modified gene into a micro-organism that overproduces the modified enzyme. The enzyme is then analyzed for increased glucose affinity, preferably as in the Example.

We substituted an amino acid residue in the active site of the enzyme which reduces steric hindrance and allows better binding to a substrate, such as D-glucose, which is larger in molecular size than the natural substrate of the enzyme, e.g. D-xylose. (When we ascribe a number to an amino acid, such as $Val_{186}$, we are referring to the amino acid numbering system of the Clostridium enzyme in references 19 and 20.) We chose to replace the $Trp_{139}$ or the $Val_{186}$ residue at the border of the substrate binding site of the wild type enzyme with Phe or Thr, respectively. We chose the $Trp_{139}$ and $Val_{186}$ residues because, as discussed above, we posit that these residues constitute the hydrophobic environment around the catalytic site.

The enzymes of the present invention have a higher affinity towards D-glucose as a substrate than xylose and, therefore, are better catalysts for the industrial production of fructose by glucose isomerization. By "higher affinity" for D-glucose, we mean that the enzyme has a lower $K_m$ and a higher $k_{cat}$ for D-glucose than does the Clostridium enzyme. $K_m$ and $k_{cat}$ are to be measured as disclosed in the Examples.

The exact mechanism by which the new glucose isomerases function is unknown, but we postulate, on the basis of results described in the Experimental section and on the basis of the information about the three-dimensional structure of Arthrobacter glucose isomerase, that the binding of D-glucose to the active site of Clostridium glucose isomerase is impaired by the Trp residue in position 139. As a result, the substitution of smaller amino acids, such as Phe or Tyr for $Trp_{139}$ allows an easier accommodation of the larger substrate molecule, D-glucose, into the active site of the enzyme.

The practice of the present invention is further illustrated by the experimental work described below.

EXAMPLES

Restriction endonucleases and enzymes for subcloning experiments were obtained from Bethesda Research Laboratories and New England Biolabs, Inc. [Alpha - $^{35}$S]-dATP (500 Ci/mmol) was obtained from Du Pont-New England Nuclear. All other chemicals were of reagent grade.

A. Site-Directed Mutagenesis

We used the technique of site-directed mutagenesis to create altered glucose isomerases. In site-directed mutagenesis, an oligonucleotide with a mismatch designed to encode the desired protein change is hybridized to a denatured or single-stranded wild-type clone. The oligonucleotide primes the clone for DNA replication, a DNA polymerase is added to the mixture, and a double-stranded DNA molecule containing the desired mutation is produced. These altered DNA molecules are transfected or transformed into a bacterium where DNA replication and protein synthesis takes place.

Specifically, we subcloned a 1.4 kb EcoRI/BamHI fragment containing the entire *C. thermosulfurogenes* xyl (glucose isomerase) gene into the M13mp19 bacteriophage vector. We isolated the fragment from the plasmid pCMG11-3 described in Lee et al. (19). *E. coli* strain HB101 (ATCC 33694, described below) was used to express the cloned gene.

Oligonucleotide primers complementary to the single-stranded template DNA were obtained from Genetic Designs, Inc., (Houston, Tex.). These primers had mismatches designed to encode the amino acids indicated in FIG. 1. SEQ ID NOs: 3-7 describe these primers. Referring to FIG. 1, $Trp_{139}$ is changed to a Phe or a Tyr residue and $Val_{186}$ is changed to a Ser or an Ala residue. The mutagenesis reaction was performed by the method of Sayers et al., (27) using a kit from Amersham Co. (Arlington Heights, Ill.). *E. coli* strain JM107 [endA1 gyrA96 thi hsdR17 supE44 relA1 delta lac-proAB /F′ treD36 proAB lacI$^q$ delta M15] (ATCC 47014) was used as host strain for site-directed mutagenesis.

After the mutagenesis reactions, we confirmed the nucleotide sequence of the altered genes. Mutant genes were then subcloned into pMMB67EH vectors and introduced into *E. coli* strain HB101 [FhsdS20 ara-14 recA13 proA12 lacY1 galK2 vpoL20 mtl-1 xyl-5] (ATCC 33694). Subcloning and nucleotide sequence determination were performed as described in Lee, et al. (19). (Lee, et al. (19) is incorporated by reference into this application as if fully set forth below). *E. coli* strain JM107 (ATCC 47014) was used as host strain for nucleotide sequence determination.

B. Characterization of the Altered Glucose Isomerases

1. Protein Isolation

The altered enzymes were purified from *E. coli* strain HB101 as described in Lee et al., (19). In brief, cells carrying recombinant plasmids were cultivated overnight and harvested the next day by centrifugation at 5000×g. The cells were washed and suspended in buffers. Cells were broken by passages through a French pressure cell and the debris removed by centrifugation. The cell extracts were stirred at 85° C. for 20 min. and then centrifuged at 12,000×g for 30 min. The soluble fractions from the heated cell extracts were loaded onto DEAE Sepharose CL-6 columns that were pre-equilibriated with buffer, and proteins were eluded with linear NaCl salt gradients (0.0–0.5 M) in the same buffer. Fractions containing significant glucose isomerase activity were pooled.

2. Enzyme Activity Determinations

Enzyme activity was determined as described previously in Lee et al., (19). In brief, reaction mixtures containing 0.8 M glucose, 10 mM $MgSO_4$, 1 mM $CoCl_2$ and the enzyme in 100 mM MOPS buffer (pH 7.0) were analyzed for the formation of fructose. For the assay of xylose isomerase activity, the reaction mixture contained 70 mM xylose, 10m $MnSO_4$ and the enzyme in 100 mM MOPS buffer (pH 0.7). After thirty minutes of incubation at 65° C., 1 ml of 0.5 M perchloric acid was added to stop the reaction. The mixture was diluted with distilled water and cysteine-carbazole-sulfuric acid reagent was added. The reaction product was measured spectrophotometrically.

Maximal activity ($V_{max}$) and $K_m$ were determined from Lineweaver-Burk plots and from Eadie-Hofstee plots as described in Fersht, et al (20). Catalytic efficiency ($k_{cat}$) was determined from the equation: $k_{cat} \cdot [E]_0 = V_{max}$, where $[E]_0$ = total enzyme concentration (assuming four active sites per tetrameric molecule).

Kinetic properties of the wild type (Clostridium) enzyme and mutant enzymes are compared below in Table 1. As shown in Table 1, substitution of $Trp_{139}$ by either Phe or Tyr decreases the $K_m$ of the mutant enzyme for glucose. In the case of $Trp_{139} \rightarrow$ Phe substitution, the mutant enzyme additionally exhibits a higher $k_{cat}$ than the wild-type enzyme. This results in a considerably higher catalytic efficiency for glucose (a three-fold increase over wild type). Moreover, the actual $V_{max}$ for glucose as a substrate is increased by a factor of 1.5 over the wild-type enzyme. At the same time, the $K_m$ for D-xylose increases and the $k_{cat}$ for D-xylose decreases.

The substitution of $Trp_{139}$ by Tyr gives a similar effect, but the increase in catalytic efficiency for D-glucose is much less pronounced. This suggests that the hydrophobic environment around the substrate-binding site may be important for the optimum catalytic functioning of the enzyme.

Another amino acid residue substitution that leads to an increased catalytic efficiency for glucose is the substitution $Val_{186}$ —> Thr. As shown in Table 1, substitution of $Val_{186}$ by Ser, a residue with a shorter side chain than Thr, but also containing a functional —OH group, has a different effect than the substitution $Val_{186}$ —> Thr. The $Val_{186}$ —> Ser substitution produces an enzyme that has a higher $K_m$ for D-glucose than the wild-type enzyme. Substitution of $Val_{186}$ by Ala actually results in a reduction of $k_{cat}$ for glucose in comparison with the wild type enzyme. These results suggest that the reason for the higher $k_{cat}$ in the Thr mutant enzyme must be the ability of $Thr_{186}$ to provide additional stabilization of the substrate through hydrogen bonding.

Still referring to Table 1, we have created mutant enzymes with two amino acid changes. One enzyme has a $Trp_{139}$ —> Phe and a $Val_{186}$ —> Thr change. The other enzyme has a $Trp_{139}$ —> Phe and a $Val_{186}$ —> Ser change. Both these enzymes have a lower $K_m$ and a higher $k_{cat}$ for glucose than the wild-type enzyme.

It will be apparent to those skilled in the art that a number of modifications and changes can be made without departing from the spirit and scope of the invention. Therefore, it is intended that the invention not be limited by the foregoing description, but only by the claims.

1. Bucke, C. (1980) in Enzymes and Food Processing (Birch, G. G., Blackebrough, N., and Parker, J. K., ed) pp. 51–72, Applied Science Publishers, London.
2. Takasaki, Y., Kosugi, U., and Kanbayashi, A. (1969) Arg. Biol. Chem. 33, 1572–1534.
3. Atrim, R. L., Colliala, W., and Schnyder, B. (1979) in *Applied Biochemistry and Bioengineering* (Wingard, L. B., ed) pp. 97–155, Academic Press, New York.
4. Chen, W. (1980) Process Biochem. 15, 30–35.
5. Chen, W. (1980) Process Biochem. 15, 36–41.
6. Carrell, H. L., Rubin, B. H., Hurley, T. J., and Glusker, J. P. (1984) J. Biol. Chem. 259, 3230–3236.
7. Farber, G. K., Petsko, G. A., and Ringe, D. (1987) *Protein Engineering* 1, 459–466.
8. Rey, F., Jenkins, J., Janin, J., Lasters, I., Alrad, P., Claessens, M., Matthyssens, G., Wodak, S. (1988) Proteins 4, 165–172.
9. Dauter, Z., Dauter, M., Hemker, J., Witzel, H., and Wilson, K. (1989) FEBS Letters 7, 1–8.
10. Batt, C. A., Claps, M. C., Bodis, M. S., Jamas, S., Sinskey, A. J. (1985) Can. J. Microbiol. 31, 930–933.
11. Schellenberg, G. D., Sarthy, A., Larson, A. E., Backer, M. P., Crabb, J. W., Lidstrom, M., Hall, B. D., and Furlong, C. E. (1984) J. Biol. Chem. 259, 6826–6832.
12. Wilhelm, M., and Hollenberg, C. P. (1984) EMBO Journal 3, 1555–2560.
13. Wilhelm, M., and Hollenberg, C. P. (1985) Nucleic Acids Res. 13, 5717–5723.
14. Shamanna, D. K., and Sanderson, K. E. (1979) J. Bacteriol. 139, 71–79.
15. Saari, G. C., Kumar, A. A., Kawasaki, G. H., Insley, M. Y., and O'hara, P. J. (1987) J. Bacteriol. 169, 612–618.
16. Drocourt, D., Bejar, S., Calmels, T., Reynes, J. P., and Tiraby, G. (1988) Nucleic Acids Res. 16, 9337.
17. Kikuchi, T., Itoh, Y., Kasumi, T. and Fukazawa, C. (1990) Agric. Biol. Chem., in press.
18. Henrick, J., Collyer, C. A, and Blow D. M. (1989) J. Mol. Biol. 208, 129–157.
19. Lee, C., Bagdasarian, M., Meng, M. H. and Zeikus, J. G. (1990) J. Biol. Chem. 265, 19082–19090.
20. Fersht, A. (1984) *Structure and Mechanisms*, W. H. Freeman and Co., New York.
21. Carrell, H. L., Glusker, J. P., Buger, V., Manfre, F., Tritsch, D., and Biellmann, J. F. (1989) Proc. Natl. Acad. Sci. USA 86, 4440–4444.
22. Faber, G. K., Glasfeld, A., Tiraby, G., Ringe, D. and Petsko, G. A. (1989) Biochemistry 28, 7289–7297.
23. Collyer, C. A., and Blow D. M. (1990) Proc. Natl. Acad. Sci. USA 87, 1362–1366.
24. Henrick, K., Collyer, C. A., and Blow, D. M. (1990) J. Mol. Biol. 212, 211–235.
25. Rose, I. A., O'Connell, E. L. and Mortlock, R. P. (1969) Biochem. Biophys. Acta 178, 376–379.
26. Rose, I. A. (1981) Philos. Trans. Royal Soc. London, Ser. B 293, 131–143.
27. Sayers, J. R., Schmidt, W., and Eckstein, F., (1988) Nucleic Acids Res. 16, 791–802.

TABLE 1

Alterations of enzymatic properties by substitutions of amino acids in the catalytic center of the *C. thermosulfurogenes* glucose isomerase.

| Enzyme | D-Glucose | | | D-Xylose | | |
|---|---|---|---|---|---|---|
| | $K_m$ (mM) | $k_{cat}$ (min$^{-1}$) | $k_{cat}/K_m$ | $K_m$ (mM) | $k_{cat}$ (min$^{-1}$) | $k_{cat}/K_m$ |
| W.T.[a] | 111 ± 7.6 | 647 ± 85 | 5.8 | 11.8 ± 2.2 | 1146 ± 106 | 97.2 |
| $Thr_{141}$ → Ser | 163 ± 19 | 465 ± 31 | 2.9 | 68 ± 12 | 1475 ± 162 | 21.7 |
| $Trp_{139}$ → Phe | 64.8 ± 7.4 | 975 ± 40 | 15 | 46.1 ± 1.1 | 626 ± 25 | 13.6 |
| $Trp_{139}$ → Tyr | 90.5 ± 12. | 540 ± 25 | 6.0 | 111.5 ± 13.2 | 359 ± 25 | 3.2 |
| $Val_{186}$ → Thr | 90.7 ± 7 | 879 ± 86 | 9.7 | 13.4 ± 1.7 | 742 ± 40 | 55.4 |
| $Val_{186}$ → Ser | 138.7 ± 7 | 793 ± 15 | 5.7 | 49 ± 8.7 | 778 ± 96. | 15.9 |
| $Val_{186}$ → Ala | 102 ± 11 | 540 ± 56 | 5.3 | 27.9 ± 0.7 | 1015 ± 15 | 36.4 |
| $Trp_{139}$ → Phe, $Val_{186}$ → Thr | 29 ± 3.7 | 954 ± 106 | 32.9 | 36 ± 2.4 | 778 ± 66 | 21.6 |
| $Trp_{139}$ → Phe | 58.4 ± 3.9 | 722 ± 20 | 12.4 | 62.8 ± 0.4 | 253 ± 5 | 4.0 |

TABLE 1-continued

Alterations of enzymatic properties by substitutions of amino acids in the catalytic center of the *C. thermosulfurogenes* glucose isomerase.

| | Substrates | | | | | |
|---|---|---|---|---|---|---|
| | D-Glucose | | | D-Xylose | | |
| Enzyme | $K_m$ (mM) | $k_{cat}$ (min$^{-1}$) | $k_{cat}/K_m$ | $K_m$ (mM) | $k_{cat}$ (min$^{-1}$) | $k_{cat}/K_m$ |
| Val$_{186}$ → Ser | | | | | | |

*W.T., wild type; } indicates double mutants.

---

We claim:

1. A genetically engineered enzyme with an amino acid sequence corresponding essentially to the *Clostridium thermosulfurogenes* glucose isomerase SEQ ID NO: 1;
wherein at least one amino acid residue selected from $Trp_{139}$ and $Val_{186}$ has been replaced by an amino acid residue having fewer atoms than the amino acid being replaced.

2. The enzyme of claim 1, wherein the $Trp_{139}$ residue has been replaced.

3. The enzyme of claim 1 wherein the $Trp_{139}$ residue has been replaced with Phe.

4. The enzyme of claim 1 wherein the $Trp_{139}$ residue has been replaced by Tyr.

5. The enzyme of claim 1 wherein the $Val_{186}$ residue has been replaced.

6. The enzyme of claim 1 wherein the $Val_{186}$ residue has been replaced by Thr.

7. The enzyme of claim 1 wherein both the $Trp_{139}$ and the $Val_{186}$ have been replaced.

8. The enzyme of claim 1 wherein $Trp_{139}$ and $Val_{186}$ residues have been replaced by Phe and Thr, respectively.

9. The enzyme of claim 1 wherein the $Trp_{139}$ and $Val_{186}$ residues have been replaced by Phe and Ser, respectively.

10. A genetically engineered glucose isomerase of improved ability to convert glucose to fructose, said isomerase being identical to a naturally occurring *Clostridium thermosulfurogenes* enzyme except that an amino acid having fewer atoms than the amino acid to be replaced has replaced either the $Trp_{139}$ residue or the $Val_{186}$ residue or both of said residues.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 439 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Clostridium thermosulfurogenes ( v i i ) IMMEDIATE SOURCE:
        ( B ) CLONE: pCMG11-3

( x ) PUBLICATION INFORMATION:
        ( A ) AUTHORS: Lee, Chanyong
            Bagdasarian, Michael
            Meng, Menghsiao
            Zeikus, J. G.
        ( B ) TITLE: Catalytic Mechanism of Xylose (Glucose)
             Isomerase from Clostridium thermosulfurogenes
        ( C ) JOURNAL: J. Biol. Chem.
        ( D ) VOLUME: 265
        ( E ) ISSUE: 31
        ( F ) PAGES: 19082-19090
        ( G ) DATE: November 5-1990
        ( K ) RELEVANT RESIDUES IN SEQ ID NO:1: FROM 1 TO 439

( x i ) SEQUENCE DESCRIPTION: SEQ ID NO:1:

```
Met Asn Lys Tyr Phe Glu Asn Val Ser Lys Ile Lys Tyr Glu Gly Pro
 1               5                  10                  15

Lys Ser Asn Asn Pro Tyr Ser Phe Lys Phe Tyr Asn Pro Glu Glu Val
             20                  25                  30

Ile Asp Gly Lys Thr Met Glu Glu His Leu Arg Phe Ser Ile Ala Tyr
         35                  40                  45

Trp His Thr Phe Thr Ala Asp Gly Thr Asp Gln Phe Gly Lys Ala Thr
     50                  55                  60

Met Gln Arg Pro Trp Asn His Tyr Thr Asp Pro Met Asp Ile Ala Lys
 65                  70                  75                  80

Ala Arg Val Glu Ala Ala Phe Glu Phe Phe Asp Lys Ile Asn Ala Pro
                 85                  90                  95

Tyr Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140
```

```
Phe  Ser  Asn  Pro  Arg  Phe  Val  His  Gly  Ala  Ser  Thr  Ser  Cys  Asn  Ala
145                 150                      155                           160

Asp  Val  Phe  Ala  Tyr  Ser  Ala  Ala  Gln  Val  Lys  Lys  Ala  Leu  Glu  Ile
               165                      170                     175

Thr  Lys  Glu  Leu  Gly  Gly  Glu  Asn  Tyr  Val  Phe  Trp  Gly  Gly  Arg  Glu
               180                      185                     190

Gly  Tyr  Glu  Thr  Leu  Leu  Asn  Thr  Asp  Met  Glu  Phe  Glu  Leu  Asp  Asn
               195                      200                     205

Phe  Ala  Arg  Phe  Leu  His  Met  Ala  Val  Asp  Tyr  Ala  Lys  Glu  Ile  Gly
210                      215                      220

Phe  Glu  Gly  Gln  Phe  Leu  Ile  Glu  Pro  Lys  Pro  Lys  Glu  Pro  Thr  Lys
225                      230                      235                           240

His  Gln  Tyr  Asp  Phe  Asp  Val  Ala  Asn  Val  Leu  Ala  Phe  Leu  Arg  Lys
                    245                      250                          255

Tyr  Asp  Leu  Asp  Lys  Tyr  Phe  Lys  Val  Asn  Ile  Glu  Ala  Asn  His  Ala
               260                      265                          270

Thr  Leu  Ala  Phe  His  Asp  Phe  Gln  His  Glu  Leu  Arg  Tyr  Ala  Arg  Ile
               275                      280                     285

Asn  Gly  Val  Leu  Gly  Ser  Ile  Asp  Ala  Asn  Thr  Gly  Asp  Met  Leu  Leu
290                           295                     300

Gly  Trp  Asp  Thr  Asp  Gln  Phe  Pro  Thr  Asp  Ile  Arg  Met  Thr  Thr  Leu
305                 310                           315                          320

Ala  Met  Tyr  Glu  Val  Ile  Lys  Met  Gly  Gly  Phe  Asp  Lys  Gly  Gly  Leu
               325                      330                          335

Asn  Phe  Asp  Ala  Lys  Val  Arg  Arg  Ala  Ser  Phe  Glu  Pro  Glu  Asp  Leu
               340                      345                     350

Phe  Leu  Gly  His  Ile  Ala  Gly  Met  Asp  Ala  Phe  Ala  Lys  Gly  Phe  Lys
               355                      360                     365

Val  Ala  Tyr  Lys  Leu  Val  Lys  Asp  Arg  Val  Phe  Asp  Lys  Phe  Ile  Glu
370                      375                      380

Glu  Arg  Tyr  Ala  Ser  Tyr  Lys  Asp  Gly  Ile  Gly  Ala  Asp  Ile  Val  Ser
385                      390                      395                          400

Gly  Lys  Ala  Asp  Phe  Arg  Ser  Leu  Glu  Lys  Tyr  Ala  Leu  Glu  Arg  Ser
                    405                      410                          415

Gln  Ile  Val  Asn  Lys  Ser  Gly  Arg  Gln  Glu  Leu  Leu  Glu  Ser  Ile  Leu
               420                      425                     430

Asn  Gln  Tyr  Leu  Phe  Ala  Glu
               435
```

( 2 ) INFORMATION FOR SEQ ID NO:2:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( x i ) SEQUENCE DESCRIPTION: SEQ ID NO:2:

```
Xaa  Xaa  Xaa  Xaa  Xaa  Xaa  Xaa  Xaa  Xaa  Xaa  Xaa  Xaa  Xaa  Xaa  Xaa  Xaa
1                   5                        10                          15

Xaa  Xaa  Xaa  Xaa  Xaa  Xaa  Xaa  Xaa  Xaa  Xaa  Xaa  Xaa  Xaa  Xaa  Xaa  Xaa
               20                       25                          30

Xaa  Xaa  Xaa  Xaa  Xaa  Xaa  Xaa  Xaa  Xaa  Xaa  Xaa  Xaa  Xaa  Xaa  Xaa  Met
               35                       40                          45
```

| | | | | | | | | | | | | | |
|---|---|---|---|---|---|---|---|---|---|---|---|---|---|
| Ser | Xaa | Gln | Xaa | Thr | Pro | Xaa | Asp | Xaa | Phe | Xaa | Phe | Gly | Leu | Trp | Thr |
| | 50 | | | | 55 | | | | 60 | | | | |
| Val | Gly | Trp | Xaa | Xaa | Arg | Asp | Xaa | Phe | Gly | Asp | Ala | Thr | Arg | Xaa | Ala |
| 65 | | | | 70 | | | | | 75 | | | | | | 80 |
| Leu | Asp | Xaa | Pro | Val | Glu | Ala | Val | Xaa | Xaa | Leu | Ala | Xaa | Leu | Gly | Ala |
| | | | | 85 | | | | | 90 | | | | | 95 |
| Xaa | Gly | Val | Thr | Phe | His | Asp | Xaa | Asp | Leu | Xaa | Pro | Phe | Gly | Xaa | Xaa |
| | | | 100 | | | | | 105 | | | | | 110 | |
| Xaa | Xaa | Glu | Arg | Xaa | Xaa | Xaa | Xaa | Glu | Xaa | Xaa | Val | Xaa | Xaa | Phe | Xaa |
| | | | 115 | | | | 120 | | | | | 125 | | |
| Xaa | Ala | Leu | Asp | Xaa | Thr | Gly | Met | Xaa | Val | Pro | Met | Xaa | Thr | Thr | Asn |
| | 130 | | | | | 135 | | | | | 140 | | | |
| Leu | Phe | Thr | His | Pro | Val | Phe | Lys | Asp | Gly | Xaa | Phe | Thr | Xaa | Asn | Asp |
| 145 | | | | | 150 | | | | | 155 | | | | | 160 |
| Arg | Asp | Val | Arg | Xaa | Tyr | Ala | Xaa | Xaa | Lys | Val | Xaa | Xaa | Xaa | Xaa | Asp |
| | | | | 165 | | | | | 170 | | | | | 175 | |
| Leu | Ala | Xaa | Glu | Leu | Gly | Ala | Xaa | Thr | Tyr | Val | Xaa | Trp | Gly | Gly | Arg |
| | | | 180 | | | | | 185 | | | | | 190 | | |
| Glu | Gly | Xaa | Glu | Xaa | Xaa | Xaa | Xaa | Asp | Lys | Xaa | Xaa | Xaa | Ala | Leu | Asp |
| | | 195 | | | | | 200 | | | | | 205 | | | |
| Arg | Met | Xaa | Glu | Xaa | Phe | Xaa | Leu | Xaa | Xaa | Xaa | Tyr | Xaa | Xaa | Xaa | Xaa |
| | 210 | | | | | 215 | | | | | 220 | | | | |
| Gly | Tyr | Xaa | Xaa | Xaa | Phe | Ala | Ile | Glu | Pro | Lys | Pro | Asn | Glu | Pro | Arg |
| 225 | | | | | 230 | | | | | 235 | | | | | 240 |
| Gly | Asp | Ile | Leu | Leu | Pro | Thr | Val | Gly | His | Xaa | Leu | Ala | Phe | Ile | Xaa |
| | | | | 245 | | | | | 250 | | | | | 255 | |
| Xaa | Leu | Glu | Xaa | Xaa | Glu | Xaa | Xaa | Gly | Asn | Tyr | Pro | Glu | Xaa | Gly | His |
| | | | 260 | | | | | 265 | | | | | 270 | | |
| Glu | Gln | Met | Ala | Gly | Leu | Asn | Phe | Xaa | His | Gly | Ile | Ala | Gln | Ala | Leu |
| | | 275 | | | | | 280 | | | | | 285 | | | |
| Trp | Xaa | Gly | Lys | Leu | Phe | His | Ile | Asp | Leu | Asn | Gly | Gln | Xaa | Gly | Xaa |
| 290 | | | | | 295 | | | | | 300 | | | | | |
| Lys | Tyr | Asp | Gln | Asp | Xaa | Xaa | Phe | Xaa | Xaa | Xaa | Xaa | Xaa | Xaa | Xaa | Ala |
| 305 | | | | | 310 | | | | | 315 | | | | | 320 |
| Phe | Xaa | Xaa | Val | Asp | Leu | Leu | Glu | Xaa | Gly | Xaa | Xaa | Xaa | Xaa | Xaa | Gly |
| | | | | 325 | | | | | 330 | | | | | 335 | |
| Xaa | Xaa | Xaa | Xaa | Xaa | Xaa | Xaa | Xaa | Xaa | Xaa | Xaa | Pro | Xaa | Xaa | Xaa | Asp |
| | | | 340 | | | | | 345 | | | | | 350 | | |
| Xaa | Xaa | Xaa | Gly | Xaa | Xaa | Xaa | Xaa | Xaa | Xaa | Xaa | Xaa | Xaa | Xaa | Xaa | Xaa |
| | | | 355 | | | | | 360 | | | | | 365 | | |
| Xaa | Ile | Xaa | Xaa | Xaa | Xaa | Xaa | Xaa | Xaa | Xaa | Xaa | Xaa | Asp | Xaa | Xaa | Ile |
| | 370 | | | | | 375 | | | | | 380 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| 385 | | | | | 390 | | | | | 395 | | | | | 400 |
| Xaa | Xaa | Xaa | Xaa | Xaa | Xaa | Xaa | Xaa | Xaa | Xaa | Xaa | Xaa | Xaa | Xaa | Xaa | Xaa |
| | | | | 405 | | | | | 410 | | | | | 415 | |
| Xaa | Xaa | Xaa | Xaa | Xaa | Xaa | Ala | Xaa | Xaa | Xaa | Xaa | Xaa | Xaa | Xaa | Xaa | Xaa |
| | | | 420 | | | | | 425 | | | | | 430 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | 435 | | | | | 440 | | | | | 445 | | | |
| Xaa | Xaa | Xaa | Xaa | Xaa | Xaa | Xaa | | | | | | | | | |
| | | 450 | | | | | 455 | | | | | | | | |

( 2 ) INFORMATION FOR SEQ ID NO:3:

( i ) SEQUENCE CHARACTERISTICS:
   ( A ) LENGTH: 27 base pairs
   ( B ) TYPE: nucleic acid
   ( C ) STRANDEDNESS: double
   ( D ) TOPOLOGY: linear ( i i ) MOLECULE TYPE: oligonucleotide ( i i i ) HYPOTHETICAL: NO ( i v ) ANTI-SENSE: NO ( x i ) SEQUENCE DESCRIPTION: SEQ ID NO:3:

ACGAAAGTTT TGTTTGGTAC TGCGAAT                27

( 2 ) INFORMATION FOR SEQ ID NO:4:

( i ) SEQUENCE CHARACTERISTICS:
      ( A ) LENGTH: 27 base pairs
      ( B ) TYPE: nucleic acid
      ( C ) STRANDEDNESS: double
      ( D ) TOPOLOGY: linear ( i i ) MOLECULE TYPE: oligonucleotide ( i i i ) HYPOTHETICAL: NO ( i v ) ANTI-SENSE: NO ( x i ) SEQUENCE DESCRIPTION: SEQ ID NO:4:

ACGAAAGTTT TGTATGGTAC TGCGAAT                27

( 2 ) INFORMATION FOR SEQ ID NO:5:

( i ) SEQUENCE CHARACTERISTICS:
      ( A ) LENGTH: 27 base pairs
      ( B ) TYPE: nucleic acid
      ( C ) STRANDEDNESS: double
      ( D ) TOPOLOGY: linear ( i i ) MOLECULE TYPE: oligonucleotide ( i i i ) HYPOTHETICAL: NO ( i v ) ANTI-SENSE: NO ( x i ) SEQUENCE DESCRIPTION: SEQ ID NO:5:

GGCGAAAACT ACACATTCTG GGGTGGA                27

( 2 ) INFORMATION FOR SEQ ID NO:6:

( i ) SEQUENCE CHARACTERISTICS:
      ( A ) LENGTH: 27 base pairs
      ( B ) TYPE: nucleic acid
      ( C ) STRANDEDNESS: double
      ( D ) TOPOLOGY: linear ( i i ) MOLECULE TYPE: oligonucleotide ( i i i ) HYPOTHETICAL: NO ( i v ) ANTI-SENSE: NO ( x i ) SEQUENCE DESCRIPTION: SEQ ID NO:6:

GGCGAAAACT ACTCATTCTG GGGTGGA                27

( 2 ) INFORMATION FOR SEQ ID NO:7:

( i ) SEQUENCE CHARACTERISTICS:
      ( A ) LENGTH: 21 base pairs
      ( B ) TYPE: nucleic acid
      ( C ) STRANDEDNESS: double
      ( D ) TOPOLOGY: linear ( i i ) MOLECULE TYPE: oligonucleotide ( i i i ) HYPOTHETICAL: NO ( i v ) ANTI-SENSE: NO ( x i ) SEQUENCE DESCRIPTION: SEQ ID NO:7:

GAAAACTACG CATTCTGGGG T                                                                 21